US012138151B2

(12) United States Patent
Ducke (10) Patent No.: US 12,138,151 B2
(45) Date of Patent: Nov. 12, 2024

(54) CONSTRAINT ARRANGEMENT FOR A STENT-GRAFT LOADED ONTO A DELIVERY SYSTEM

(71) Applicant: Cook Medical Technologies LLC, Bloomington, IN (US)

(72) Inventor: Werner Dieter Ducke, Queensland (AU)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 236 days.

(21) Appl. No.: 17/682,722

(22) Filed: Feb. 28, 2022

(65) Prior Publication Data

US 2022/0280280 A1 Sep. 8, 2022

(30) Foreign Application Priority Data

Mar. 2, 2021 (AU) ................. 2021201336

(51) Int. Cl.
*A61F 2/07* (2013.01)
*A61F 2/95* (2013.01)

(52) U.S. Cl.
CPC ............ *A61F 2/07* (2013.01); *A61F 2/95* (2013.01); *A61F 2002/9511* (2013.01); *A61F 2220/0075* (2013.01)

(58) Field of Classification Search
CPC .. A61F 2/04; A61F 2/062; A61F 2/064; A61F 2002/065; A61F 2002/067;
(Continued)

(56) References Cited

U.S. PATENT DOCUMENTS 7,537,606 B2 5/2009 Hartley et al.
8,172,895 B2 5/2012 Anderson et al.
(Continued)

FOREIGN PATENT DOCUMENTS

EP 0664107 A1 7/1995
EP 3320881 B1 5/2018
(Continued)

OTHER PUBLICATIONS

European Search Report for corresponding EP Application No. 22155713.5 dated Aug. 19, 2022, 6 pages.

*Primary Examiner* — Yashita Sharma
(74) *Attorney, Agent, or Firm* — Crowell & Moring LLP (57) ABSTRACT

A constraint arrangement for a stent-graft loaded onto a delivery system having a suture extending circumferentially around a surface of a graft from a first fixed end fixed to a stent-graft to a positionable region, and through the graft at a first constraining perforation into the lumen and returning out of the lumen to the surface of the graft at a second constraining perforation to a second fixed end fixed to the stent-graft, thereby forming a loop of the suture within a lumen of the graft, the loop wrapped circumferentially around a cannula such that a pair of legs of the loop hold the positionable region with respect to the cannula, wherein a bight of the loop extends through a gap between the legs and wherein the release wire extends through the bight thereby capturing the bight and releasably securing the loop around the cannula.

20 Claims, 10 Drawing Sheets (58) Field of Classification Search
CPC .................. A61F 2002/068; A61F 2/07; A61F 2002/072; A61F 2002/075; A61F 2002/077; A61F 2002/9511; A61F 2/82; A61F 2/856
See application file for complete search history.

(56) References Cited

U.S. PATENT DOCUMENTS

| | | | |
|---|---|---|---|
| 8,377,113 | B2 | 2/2013 | Hartley et al. |
| 8,597,346 | B2 | 12/2013 | Hartley et al. |
| 8,603,156 | B2 | 12/2013 | Hartley et al. |
| 8,728,148 | B2 | 5/2014 | Roeder et al. |
| 8,758,425 | B2 | 6/2014 | Greenberg et al. |
| 8,864,808 | B2 * | 10/2014 | Greenberg .............. A61F 2/954 623/1.11 |
| 8,926,686 | B2 | 1/2015 | King |
| 8,979,919 | B2 | 3/2015 | Goddard et al. |
| 9,101,506 | B2 | 8/2015 | Arbefeuille et al. |
| 9,198,787 | B2 | 12/2015 | Kratzberg et al. |
| 9,226,814 | B2 | 1/2016 | Jensen et al. |
| 9,278,018 | B2 | 3/2016 | Roeder |
| 9,504,555 | B2 | 11/2016 | Hartley et al. |
| 10,172,731 | B2 | 1/2019 | Roeder |
| 10,231,858 | B2 | 3/2019 | Wilger et al. |
| 10,350,096 | B2 | 7/2019 | Roeder |
| 10,905,575 | B2 | 2/2021 | Roeder |
| 2008/0262596 | A1 * | 10/2008 | Xiao .................. A61B 17/0682 623/1.14 |
| 2010/0179636 | A1 | 7/2010 | Mayberry et al. |
| 2013/0116773 | A1 * | 5/2013 | Roeder ..................... A61F 2/07 623/1.35 |
| 2014/0148895 | A1 | 5/2014 | King |
| 2017/0189212 | A1 * | 7/2017 | Eller ....................... A61F 2/844 |
| 2018/0153721 | A1 * | 6/2018 | McHugo ................ A61F 2/966 |
| 2018/0168838 | A1 | 6/2018 | Kratzberg et al. |
| 2019/0192323 | A1 | 6/2019 | Cully et al. |
| 2019/0231571 | A1 | 8/2019 | Lostetter |
| 2019/0269498 | A1 * | 9/2019 | Arbefeuille ............... A61F 2/95 |
| 2021/0052364 | A1 | 2/2021 | Guo et al. |

FOREIGN PATENT DOCUMENTS

| | | |
|---|---|---|
| WO | WO 03/034948 A1 | 5/2003 |
| WO | WO 2004/017868 A1 | 3/2004 |

* cited by examiner

CONSTRAINT ARRANGEMENT FOR A STENT-GRAFT LOADED ONTO A DELIVERY SYSTEM

This patent application claims the benefit of priority to Australian Patent Application No. 2021201336, filed Mar. 2, 2021, and entitled "A Constraint Arrangement for a Stent Graft Loaded Onto a Delivery System," the entire contents of which is incorporated herein by reference in its entirety.

BACKGROUND

1. Field of Disclosure

This disclosure relates to medical devices and more particularly to stent-grafts mountable onto a deployment device for endovascular introduction.

2. Background of the Disclosure

This disclosure is directed to grafts, stents, and stent-grafts for placement into the aorta for the treatment of aneurysms. The disclosure, however, is not so restricted and may be applied to grafts, stents, and stent-grafts for placement in any lumen of the human or animal body.

The accurate positioning of stent-grafts is important for a number of reasons, including in many cases the need to avoid occlusion of branch arteries. The diameter of a stent-graft is typically deliberately made larger than the diameter into which it is to be placed to allow for accurate sealing against the vessel wall, possible errors in sizing and subsequent relaxation of the vessel wall. Once released from a delivery device, a stent-graft with self-expanding stents will take up a position against the vessel wall and it will be difficult if not impossible to reposition it. Many cases of aneurism repair require the accurate placement of stent-graft features such as a fenestration or scallop.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels, similar terms such as caudal and cranial should be understood.

BRIEF SUMMARY

According to a first aspect of the disclosure, there is provided a constraint arrangement for a stent-graft loaded onto a delivery system, the stent-graft having a graft defining an elongate lumen, a plurality of stents and at least one positionable region adjacent to a feature, the delivery system having a cannula and a release wire, the constraint arrangement comprising: a suture extending circumferentially around an outside surface of the graft from a first fixed end fixed to the stent-graft to the positionable region, and through the graft at a first constraining perforation into the lumen and returning out of the lumen to the outside surface of the graft at a second constraining perforation to a second fixed end fixed to the stent-graft, thereby forming a loop of the suture within the lumen, the loop wrapped circumferentially around the cannula such that a pair of legs of the loop hold the positionable region with respect to the cannula, wherein a bight of the loop extends through a gap between the legs and wherein the release wire extends through the bight thereby capturing the bight and releaseably securing the loop around the cannula.

The release wire may be retractable from the bight of the loop thereby releasing the bight such that the positionable region is not held with respect to the cannula. The constraint arrangement may be arranged and constructed such that expansion of the stent-graft, when the release wire is in the retracted condition, increases the circumferential length between the fixed end of the suture and the constraining perforation thereby creating tension in the suture, the tension acting to retract the loop towards an inner surface of the graft.

The suture penetrates through the graft into and then out of the lumen at least once between the first fixed end and the first constraining perforation.

The release wire may repeatedly loop over the cannula along a longitudinal length of the stent-graft thereby securing the stent-graft to the cannula at a plurality of space-apart locations.

The release wire may repeatedly penetrate the graft from within the lumen to an outside of the lumen and then penetrates the graft from the outside of the lumen to within the lumen. The release wire may be disposed helically along the length of the stent-graft.

The suture may extend circumferentially around an outside surface of the graft over at least 45 degrees of arc from the fixed end fixed to the stent-graft to the positionable region, when the release wire has been retracted and the positionable region is not held with respect to the cannula. The suture may extend circumferentially around an outside surface of the graft over at least 75 degrees of the arc from the fixed end fixed to the stent-graft to the positionable region, when the release wire has been retracted and the positionable region is not held with respect to the cannula.

In one embodiment, the feature is a fenestration. In another embodiment, the feature is a scalloped region.

According to a another aspect of the disclosure, there is provided a constraint arrangement for a stent-graft loaded onto a delivery system, the stent-graft having a graft defining an elongate lumen, a plurality of stents and at least one positionable region adjacent to a feature, the delivery system having a cannula and a release wire, the constraint arrangement comprising: a first suture extending circumferentially around an outside surface of the graft from a first fixed end fixed to the stent-graft to the positionable region, and through the graft and into the lumen and returning out of the lumen to the outside surface of the graft to a second fixed end fixed to the stent-graft, thereby forming a first loop of the first suture within the lumen, a second suture extending circumferentially around the outside surface of the graft from a third fixed end fixed to the stent-graft to the positionable region, and into the lumen and returning out of the lumen to the outside surface of the graft to a fourth fixed end fixed to the stent-graft, thereby forming a second loop of the second suture within the lumen, the second loop wrapped circumferentially around the cannula such that a second pair of legs of the second loop and a first pair of legs of the first loop hold the positionable region with respect to the cannula, wherein a bight of the second loop extends through a gap between the first pair of legs of the first loop, and wherein the release wire extends through the bight thereby capturing the bight and releaseably securing the first loop and the second loop around the cannula.

The release wire may be retractable from the bight thereby releasing the bight such that the positionable region is not held with respect to the cannula. The constraint arrangement may be arranged and constructed such that expansion of the stent-graft, when the release wire is in the retracted condition, increases the circumferential length between the fixed end of the first suture and the positionable region thereby creating tension in the first suture, the tension acting to retract the first loop towards an inner surface of the graft.

The feature may be a fenestration. The feature may be a scalloped region.

A detailed description of one or more embodiments of the disclosure is provided below along with accompanying figures that illustrate by way of example the principles of the invention. While the invention is described in connection with such embodiments, it should be understood that the invention is not limited to any embodiment. On the contrary, the scope of the invention is limited only by the appended claims and the invention encompasses numerous alternatives, modifications and equivalents. For the purpose of example, numerous specific details are set forth in the following description in order to provide a thorough understanding of the present invention.

The present invention may be practiced according to the claims without some or all of these specific details. For the purpose of clarity, technical material that is known in the technical fields related to the invention has not been described in detail so that the present invention is not unnecessarily obscured.

BRIEF DESCRIPTION OF THE DRAWINGS

This then generally describes the invention but, to assist with understanding, reference will now be made to the accompanying drawings which show preferred embodiments of the invention.

DETAILED DESCRIPTION OF THE DRAWINGS AND THE PRESENTLY PREFERRED EMBODIMENTS

Figure 1A:
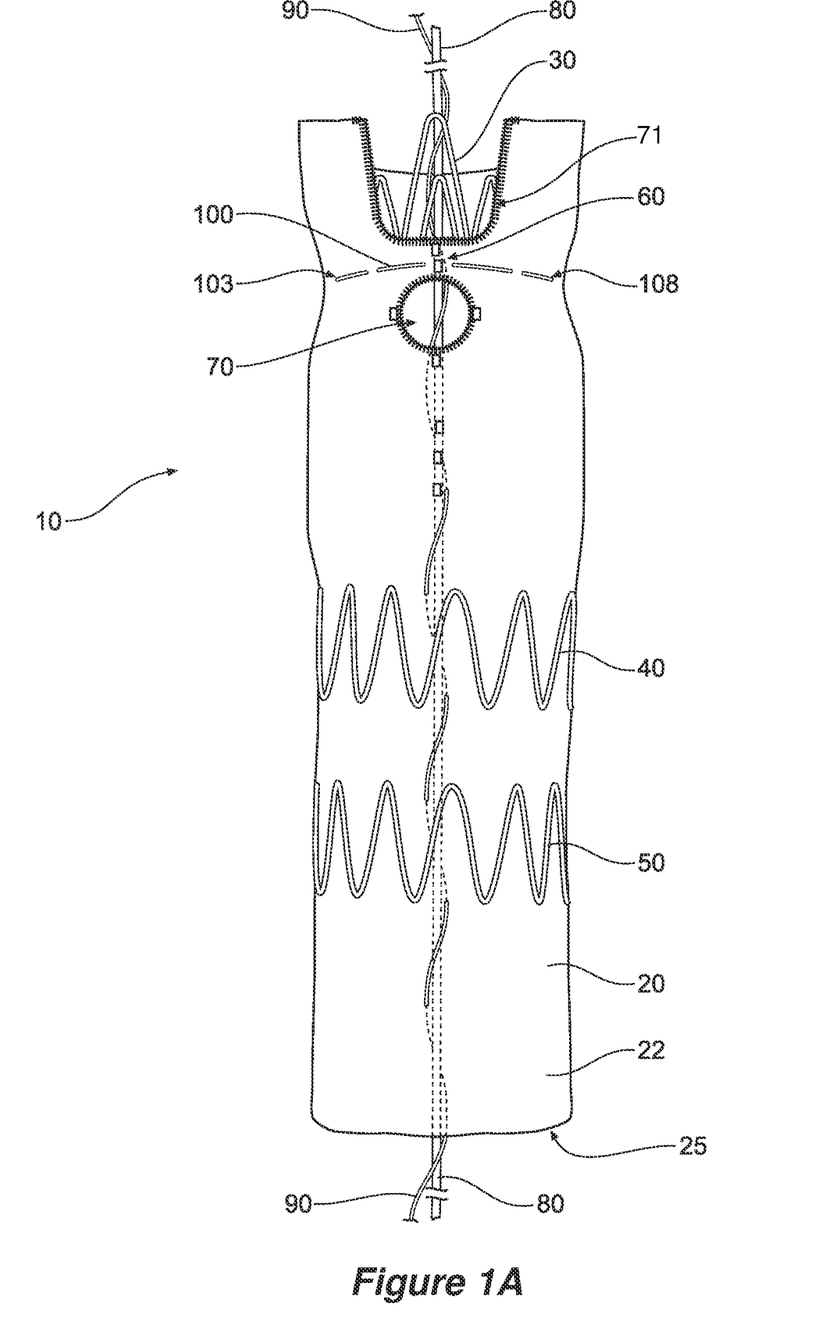
FIG. 1A is a front view of a constraint arrangement for a stent-graft loaded onto a delivery system.

Referring to FIG. 1A, a constraint arrangement for a stent-graft 10 loaded onto a delivery system according to a first embodiment of the disclosure is shown. The stent-graft has a graft 20 defining an elongate lumen 25, a plurality of stents 30, 40, 50 and at least one positionable region 60 adjacent to a feature, such as a fenestration 70. The delivery system has a cannula 80 and a release wire 90.

Figure 3:
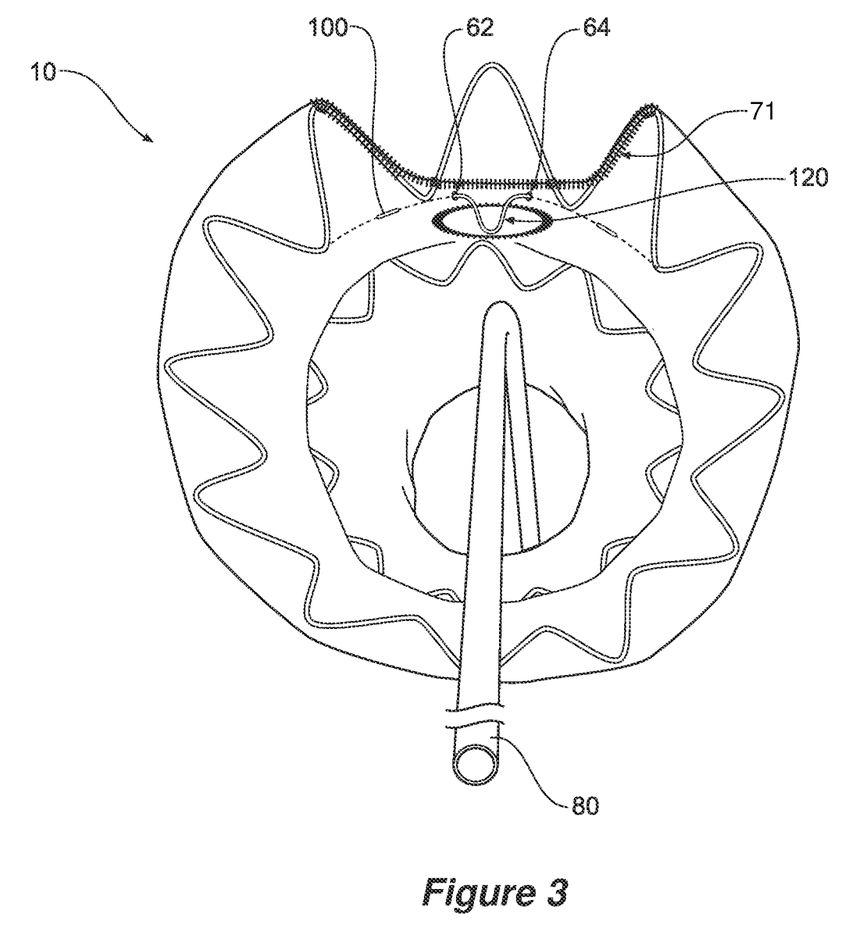
FIG. 3 is a further view of the stent-graft shown in FIG. 1A, again from inside the lumen, prior to securement.

Now referring to FIGS. 1A, 2A, 2B and 3, it can be seen that the constraint arrangement comprises: a suture 100 extending circumferentially around an outside surface 22 of the graft from a first fixed end 103 fixed to the stent-graft to the positionable region 60, and through the graft 20 at a first constraining perforation 62 into the lumen and returning out of the lumen to the outside surface of the graft at a second constraining perforation 64 to a second fixed end 108 fixed to the stent-graft 10. A loop 120 of the suture is formed within the lumen. This loop 120 is shown in FIG. 3.

Figure 4:
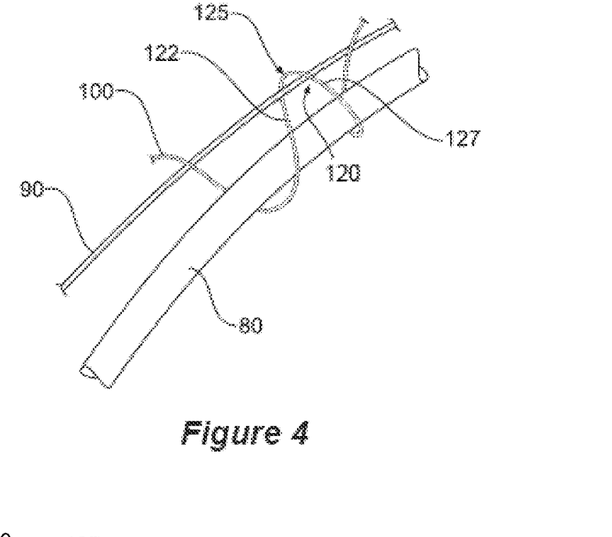
FIG. 4 is a close-up view of a portion of the constraint arrangement of FIGS. 1A, 2A, 2B and 3.
Figure 5A:
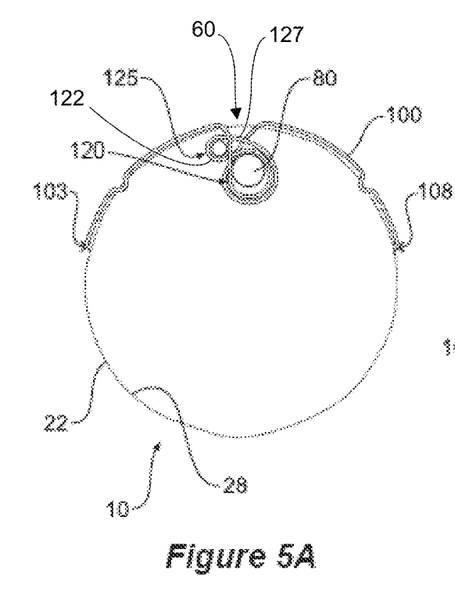
FIGS. 5A and 5B are diagrammatic views showing routing of the suture shown in FIG. 1A in a constraining and non-constraining condition respectively.

Referring to FIGS. 4 and 5A, it can be seen that the loop 120 is wrapped circumferentially around the cannula 80 such that a pair of legs 122, 127 of the loop (most clearly shown in FIG. 4) hold the positionable region 60 with respect to the cannula 80. A bight 125 of the loop 120 extends through a gap between the legs 122, 127 and the release wire 90 extends through the bight 125 thereby capturing the bight 125. Thus, the release wire 90 releaseably secures the loop 120 around the cannula 80.

Referring to FIG. 4, read with FIG. 5A, the routing of the suture 100 with respect to the cannula 80 and the release wire 90 is clearly shown before tightening. As can be seen in FIG. 5A, the graft 20 is securely held on the cannula 80 at a specific location or positionable region 60. Typically, this positionable region 60 will be at, or adjacent to, an important feature of the stent-graft 10, such as a fenestration 70 or a scallop 71 (shown in FIGS. 1A and 1B). The positionable region 60 is named a 'positionable' region, because it is positionable by the clinician through manipulation of a handle connected to the cannula 80.

Figure 5B:
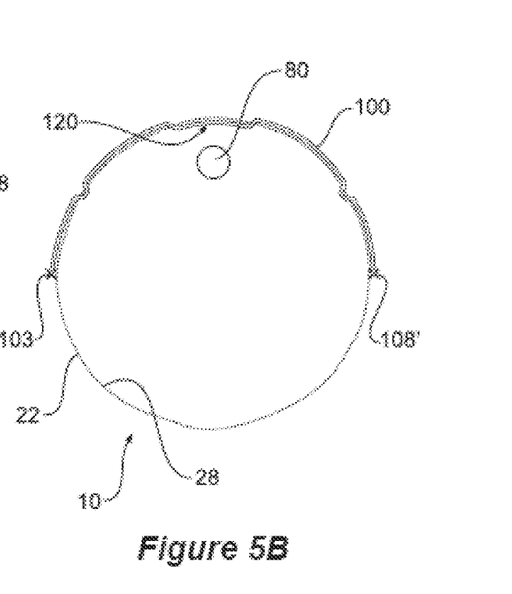

The release wire 90 is retractable from the bight 125 of the loop 120 thereby releasing the bight 125 such that the positionable region 60 is no longer held with respect to the cannula 80, as is shown in FIG. 5B.

Using the constraint arrangement for a stent-graft described above, a certain portion of a stent-graft 10 can be controlled more accurately for positioning and alignment purposes. This assists clinicians in various ways. For instance, it assists clinician conducting endovascular procedures for aneurism repair which require the accurate placement of stent-graft features such as a fenestration or scallop 71.

The ability to releasably constrain a required stent-graft feature, such as a fenestration, by utilizing existing components, such as a release or trigger wire is useful and helps keep the overall apparatus that is introduced into the vascular system of patient compact.

Considering FIGS. 5A and 5B together, it can be seen that the constraint arrangement is arranged and constructed such that expansion of the stent-graft 10, when the release wire is in the retracted condition, increases the circumferential length between the fixed end 103 of the suture 100 and the constraining perforation 62 (as shown on FIG. 3) thereby creating tension in the suture 100. This tension acts to retract the loop 120 towards an inner surface 28 of the graft. This reduces the length of suture within the lumen and also reduces the likelihood of interference with normal blood slow once the procedure of delivering the stent-graft into a patient's anatomy is complete.

The suture 100 penetrates though the graft 20 into and then out of the lumen 25 at least once between the first fixed end 103 and the first constraining perforation 62 as can be seen reading FIGS. 1A and 3 together. With the embodiment shown in FIG. 1A, most of the suture remains on the outside surface 22 of the stent-graft 10, thereby advantageously minimizing the length of suture within the lumen 25.

Again, referring to FIG. 1A, it can be seen that the release wire 90 repeatedly loops over the cannula 80 along a longitudinal length of the stent-graft 10 thereby securing the stent-graft 10 to the cannula 80 at a plurality of spaced-apart locations. With the embodiment illustrated, the release wire repeatedly penetrates the graft from within the lumen to the outside of the lumen and then penetrates the graft from the outside of the lumen to within the lumen. The release wire is disposed helically along the length of the stent-graft, as can be seen in FIG. 1A.

The release wire 90 retains the stent-graft to the cannula, or to a guide wire catheter, and includes a wire wound around the cannula and through the material of the stent-graft in a helical or spiral manner as described above and as illustrated in FIG. 1A. The pitch of the helically wound release wire 90 can be between 20 to 40 mm for example. The release wire 90 extends to a handle for instance, the handle manipulable by a clinician.

The suture 100 extends circumferentially around an outside surface 22 of the graft over at least 45 degrees of arc from the fixed end 103 fixed to the stent-graft 10 to the positionable region 60 when the release wire has been retracted and the positionable region is not held with respect to the cannula, such as is shown in FIG. 5B. In the embodiment illustrated in FIGS. 1A, 5A and 5B, the suture extends circumferentially around an outside surface 22 of the graft over at least 75 degrees of arc from the fixed end 103 fixed to the stent-graft to the positionable region, when the release wire has been retracted and the positionable region is not held with respect to the cannula.

Figure 1B:
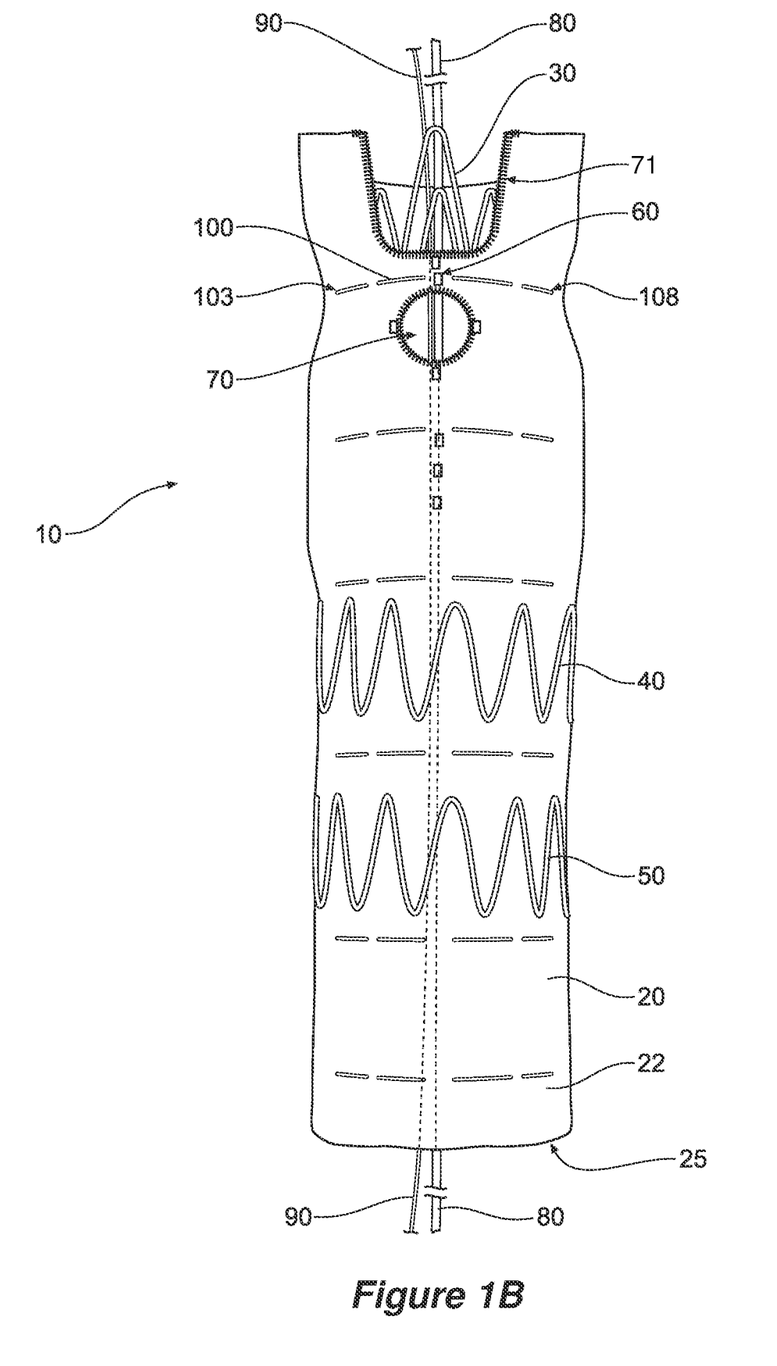
FIG. 1B is a front view of another constraint arrangement for a stent-graft loaded onto a delivery system.
Figure 2A:
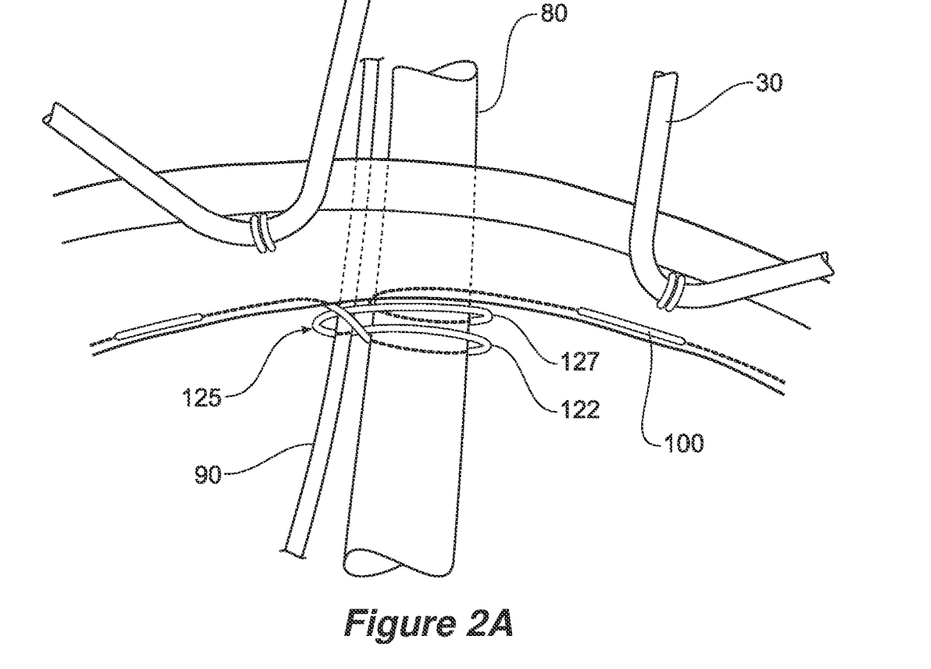
FIG. 2A is a close-up view of FIG. 1A from within a lumen of the stent-graft, showing routing of a suture being tied around a cannula.
Figure 2B:
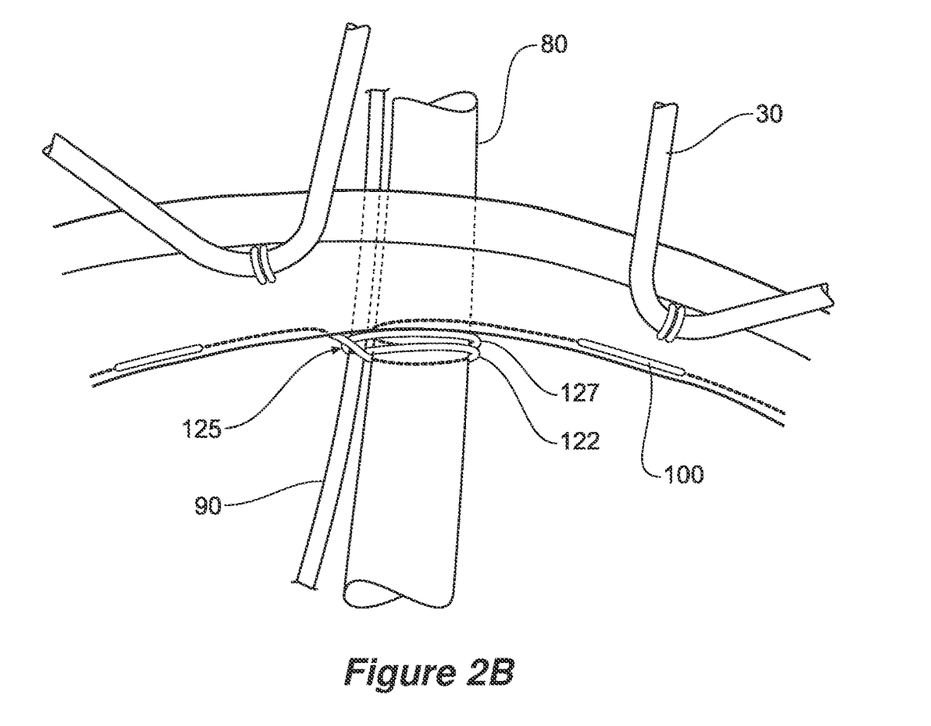
FIG. 2B is a similar view to that of FIG. 2A, but with the suture tightened.

In another embodiment of the disclosure, shown in FIG. 1B, a helically wound release wire is not employed. Instead, the release wire is relatively straight and attachment of the stent-graft 10 to the cannula along the length of the stent-graft 10 is achieved by using a plurality of sutures, each suture sewn like the suture 100 as described above.

Figure 10:
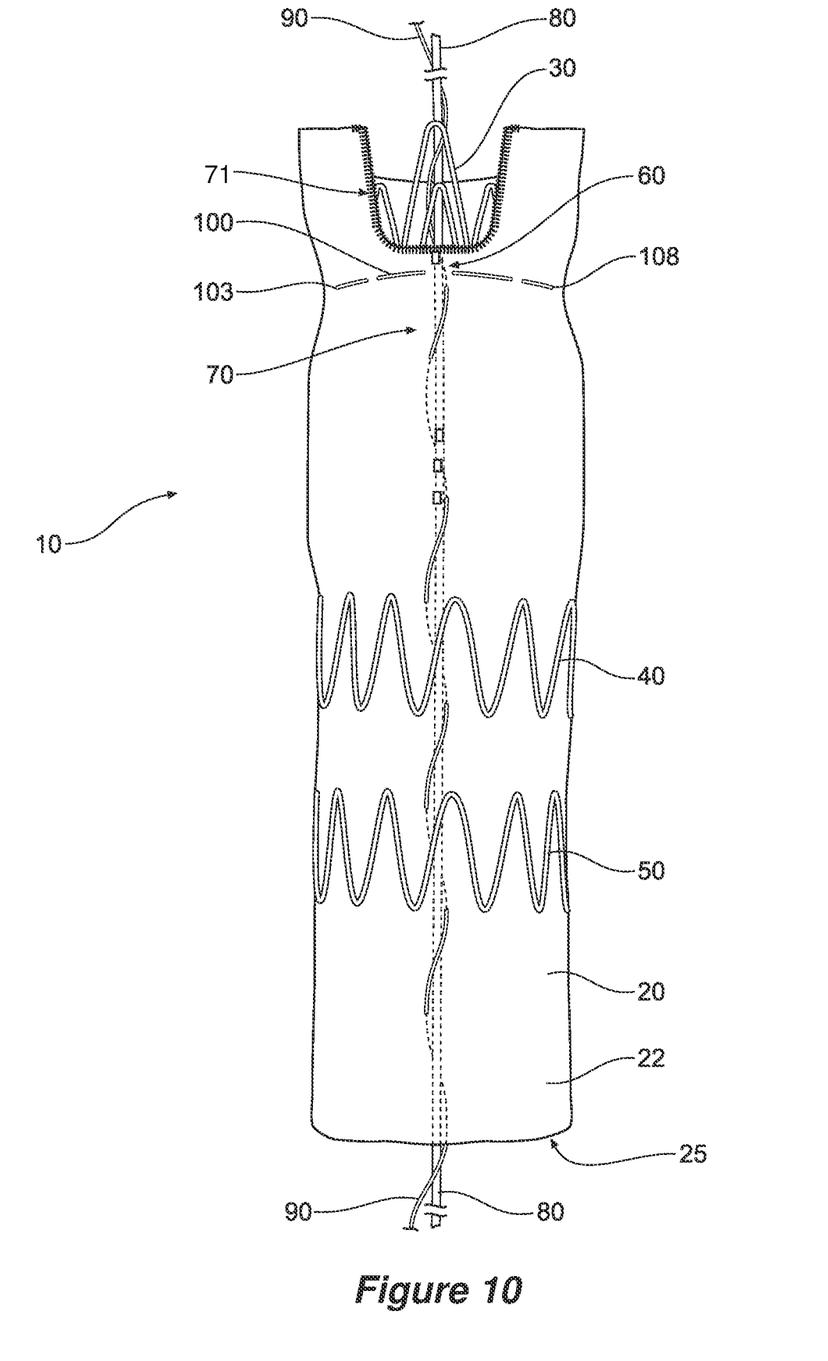
FIG. 10 is a front view of a constraint arrangement for an alternative stent-graft loaded onto a delivery system.

Referring now to FIG. 10, a positionable region is adjacent to a scallop 71, allowing the clinician to precisely control the position of the scallop 71. In other respects, the constraint arrangement is generally the same as that shown in FIGS. 1A, 1B, 2A, 2B, 3, 4, 5A and 5B, where the positionable region is adjacent to a fenestration.

Figure 7:
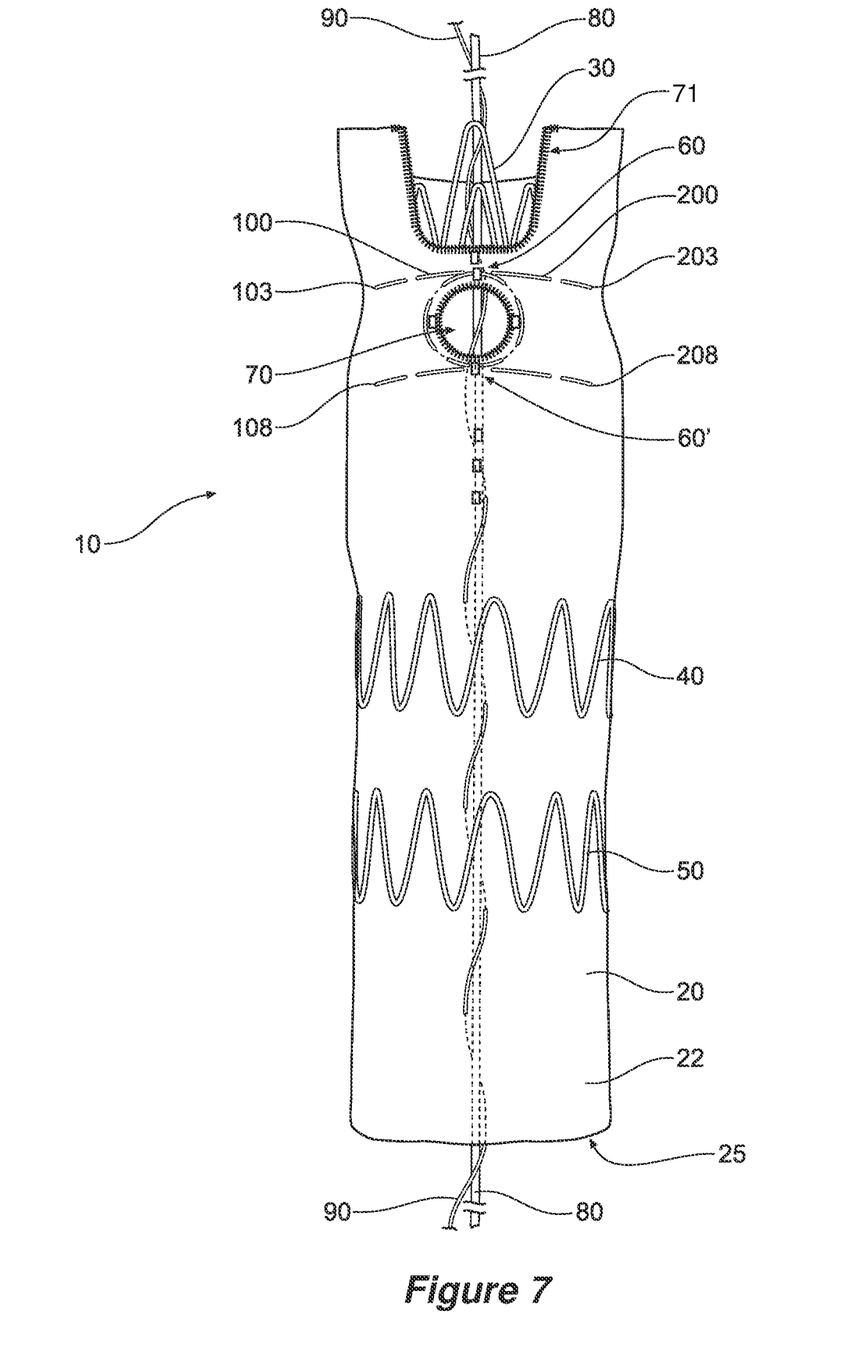
FIG. 7 is a front view of an alternative constraint arrangement for a stent-graft loaded onto a delivery system, according to a second aspect of the disclosure.

A second embodiment of the disclosure is shown in FIGS. 7 to 9B. In FIG. 7, a constraint arrangement for a stent-graft 10 loaded onto a delivery system is shown. The stent-graft has a graft 20 defining an elongate lumen 25, a plurality of stents 30, 40, 50 and at least one positionable region 60 adjacent to a feature 70. The delivery system has a cannula 80 and a release wire 90. The constraint is similar to that of the constraint arrangement of the first embodiment of the disclosure in many ways, but differs in that two loops of suture are employed, rather than one, for each securement. Specifically, the constraint arrangement comprises a first suture 100 extending circumferentially around an outside surface 22 of the graft from a first fixed end 103 fixed to the stent-graft to the positionable region, and through the graft and into the lumen and returning out of the lumen to the outside surface of the graft to a second fixed end 108 fixed to the stent-graft, thereby forming a first loop 120 of the first suture 100 within the lumen. This can be seen in FIGS. 9A and 9B where the first loop 120 is wrapped circumferentially (part circumferentially) around the cannula 80 such that a first pair of legs 122, 127 of the first loop 120 hold the positionable region 60 with respect to the cannula 80.

Figure 9A:
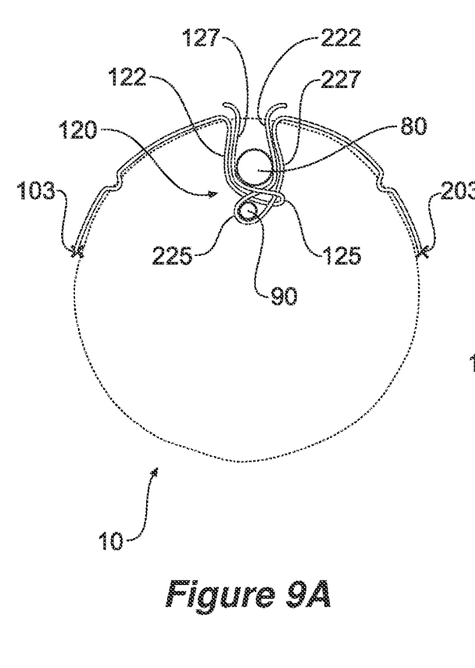
FIGS. 9A and 9B are diagrammatic views showing routing of the suture shown in FIG. 7 in a constraining and non-constraining condition respectively.
Figure 9B:
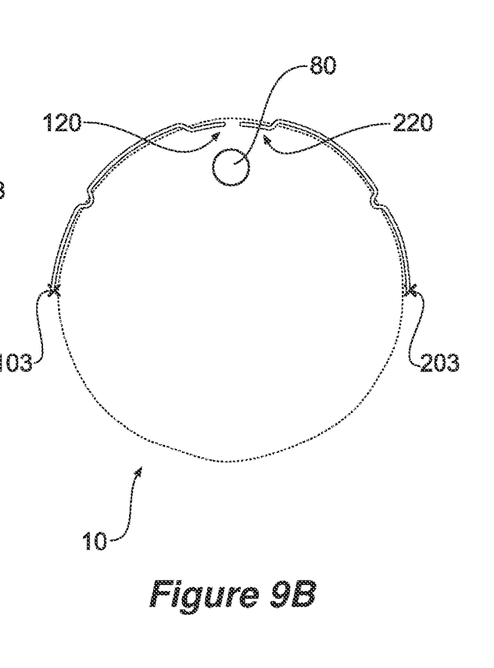

A second suture 200 also extends circumferentially (part circumferentially) around the outside surface 22 of the graft from a third fixed end 203 fixed to the stent-graft to the positionable region 60, and into the lumen 25 and returning out of the lumen 25 to the outside surface 22 of the graft to a fourth fixed end 208 fixed to the stent-graft, thereby forming a second loop 220 of the second suture within the lumen 25.

A second loop formed by the second suture is wrapped circumferentially around the cannula, such that a second pair of legs 222, 227 of the second loop 220 and a first pair of legs 122, 127 of the first loop 120 hold the positionable region 60 with respect to the cannula. A bight 225 of the second loop 220 extends through a gap between the first pair of legs 122, 127 of the first loop 120. The release wire 90 extends through the bight 225 thereby capturing the bight 225 and releasably secures the first loop 120 and the second loop 220 around the cannula.

Figure 8:
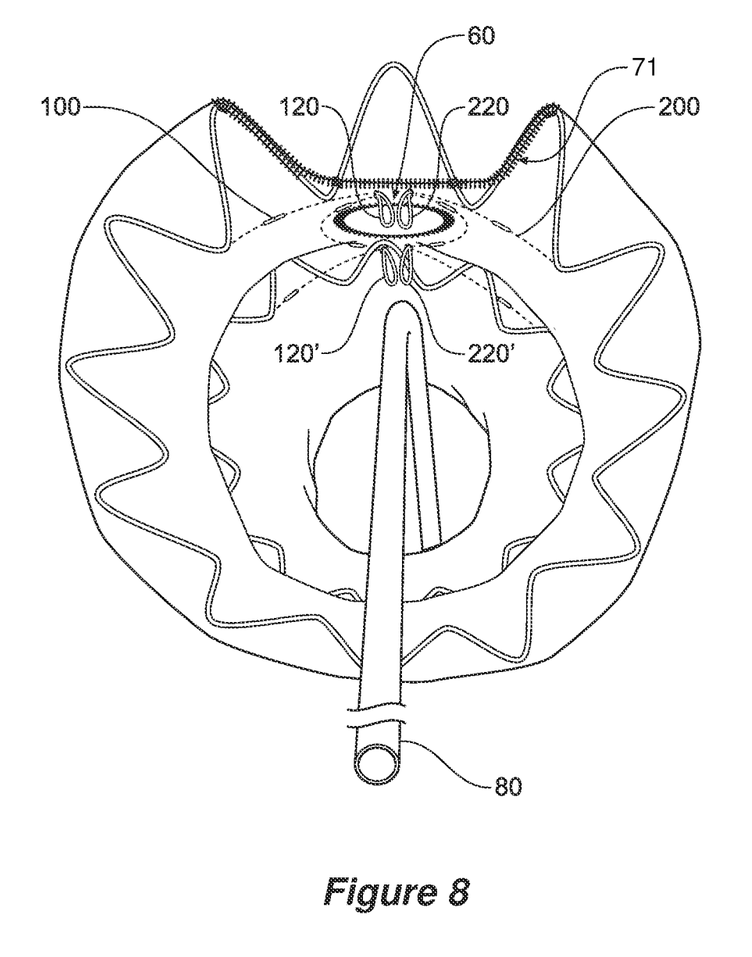
FIG. 8 is a further view of the stent-graft shown in FIG. 7, from inside the lumen, prior to securement.

Referring to FIGS. 7 and 8, it can be seen that with this second embodiment there is also a second positionable region 60' located on the other side of a feature in the form of a fenestration 70. This second positionable region 60' is held to the cannula 80, providing further control to the clinician. It should be noted however that the double loop arrangement may be employed at just one positionable region 60 if desired.

Figure 6A:
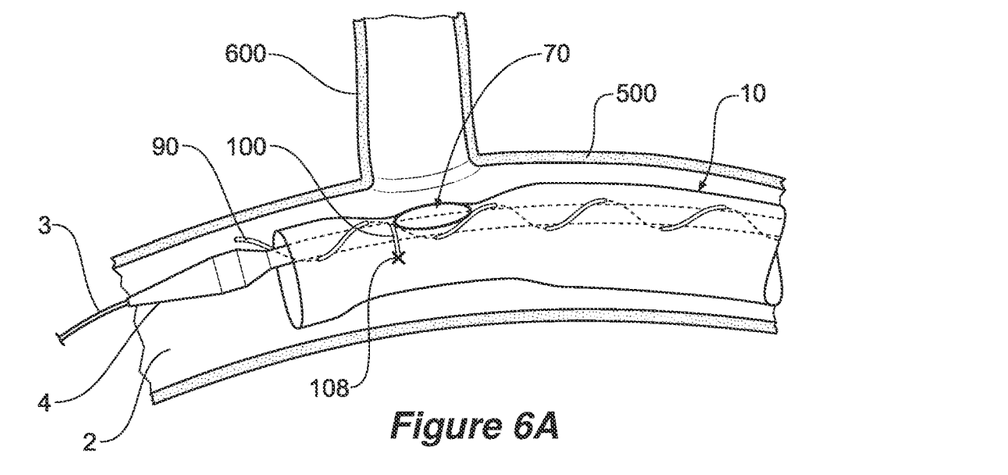
FIGS. 6A, 6B and 6C are progressive illustrations showing the constraint arrangement of the previous figures being deployed and then released within a lumen of a patient.
Figure 6B:
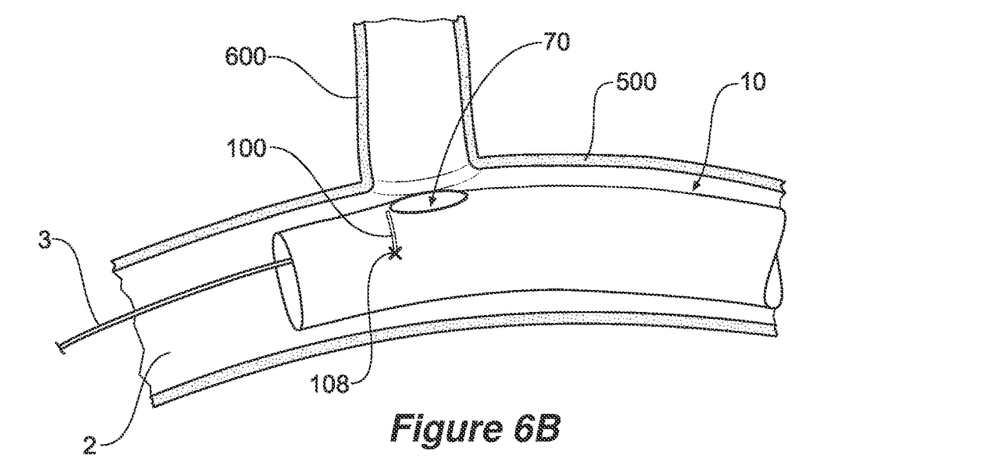
Figure 6C:
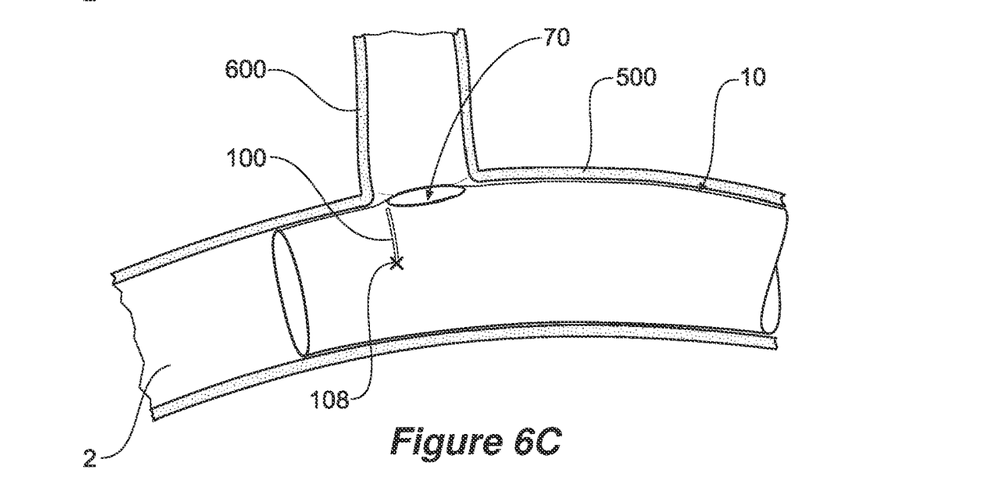

With all of the embodiments described above, the suture loops are greatly reduced (retracted) when the stent-graft is fully released and ballooned, as is shown progressively in FIGS. 6A to 6C. For example, this is achieved in the embodiment illustrated in FIGS. 1A to 5B by firstly weaving the loop material circumferentially around the stent-graft material for about 90 degrees either side of the feature, keeping it firm, but without reducing the stent-graft diameter, or at least not reducing it substantially, and then pulling the loop from the area of the feature that requires constraining. This way, the loop resumes its retracted condition along the circumference of the stent-graft after the stent-graft is released.

Now referring to the embodiment illustrated in FIG. 1A again, a deployment sequence for the constraint arrangement will be described with reference to FIGS. 6A to 6C.

FIG. 6A shows the constraint arrangement within a lumen 2 of a patient in a position where the feature, in this case a fenestration 70, is aligned with a target branch lumen 600 that branches from a main lumen 500. Typically, the constraint arrangement and the stent-graft 10 will have reached this position using the Seldinger technique. This technique involves creating a surgical opening in the vascular system linked to the vessel of interest with a needle and inserting a wire guide into the vessel through a bore of the needle. For example, the femoral artery may be used to access the aorta. The needle can be withdrawn, leaving the wire guide in place. A delivery device is then inserted over the wire guide and into the vessel. The delivery device may be used in conventional fashion to insert into the blood vessel a stent-graft or other prostheses or devices. In FIG. 6A, a guide wire 3 is shown over which a nose cone dilator 4 slides. Adjacent to the nose cone dilator 4 is the stent-graft 10 held to the cannula 80 by a helically wound release wire 90. The constraint arrangement described above with reference to FIGS. 1A, 2A, 2B, 3, 4, 5A and 5B is also partly visible in this Figure, with suture 100 and its first fixed end 103 clearly visible.

While in the position within the main lumen 500, which may be the aorta for instance, the clinician can manipulate the position of the fenestration 70 to align precisely with the opening of the branch lumen 600 (for example a renal artery). The clinician may then cannulate the target vessel with a wire and catheter prior to the final positioning and release of the stent-graft. Once this is complete, the release wire 90 can be retracted, releasing the positionable region 60 adjacent to the fenestration 70 and progressively releasing the stent-graft 10 from the cannula 80 until the position shown in FIG. 6B is attained.

In a final step, the stent-graft 10 is typically further expanded by the deployment of a balloon from within the lumen 25 of the stent-graft 10 until the stent-graft 10 reaches the position shown in FIG. 6C.

During the above step, the suture loop 120, or each suture loop is further retracted as the circumference of the stent-graft 10 increases.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A constraint arrangement for a stent-graft loaded onto a delivery system, the stent-graft having a graft defining an elongate lumen, a plurality of stents and at least one positionable region adjacent to a feature, the delivery system having a cannula and a release wire, the constraint arrangement comprising:
    at least one suture extending at least partially circumferentially around a surface of the graft from a first fixed end fixed to the stent-graft to the positionable region, and through the graft at a first constraining perforation into the lumen and returning out of the lumen to the surface of the graft at a second constraining perforation to a second fixed end fixed to the stent-graft and circumferentially spaced from the first fixed end, thereby forming a loop portion of the at least one suture within the lumen,
    the loop portion wrapped circumferentially around the cannula such that a pair of legs of the loop hold the positionable region with respect to the cannula,
    wherein a bight of the loop portion extends through a gap between the legs and wherein the release wire extends through the bight thereby capturing the bight and releasably securing the loop portion around the cannula.

2. The constraint arrangement of claim 1, wherein the release wire is retractable from the bight of the loop portion thereby releasing the bight such that the positionable region is not held with respect to the cannula.

3. The constraint arrangement of claim 2, wherein the expansion of the stent-graft, when the release wire is in the retracted condition, increases the circumferential length between the first fixed end of the suture and the first constraining perforation thereby creating tension in the suture, the tension acting to retract the loop portion towards an inner surface of the graft.

4. The constraint arrangement of claim 3, wherein the suture penetrates through the graft into and then out of the lumen at least once between the first fixed end and the first constraining perforation.

5. The constraint arrangement of claim 4, wherein the release wire repeatedly loops over the cannula along a longitudinal length of the stent-graft thereby securing the stent-graft to the cannula at a plurality of longitudinally space-apart locations.

6. The constraint arrangement of claim 5, wherein the release wire repeatedly penetrates the graft from within the lumen to an outside of the lumen and then penetrates the graft from the outside of the lumen to within the lumen.

7. The constraint arrangement of claim 5, wherein the release wire is disposed helically along the length of the stent-graft.

8. The constraint arrangement of claim 1, wherein the suture extends circumferentially around an outside surface of the graft over at least 45 degrees of arc from the fixed end fixed to the stent-graft to the positionable region, when the release wire has been retracted and the positionable region is not held with respect to the cannula.

9. The constraint arrangement of claim 1, wherein the suture extends circumferentially around an outside surface of the graft over at least 75 degrees of the arc from the fixed end fixed to the stent-graft to the positionable region, when the release wire has been retracted and the positionable region is not held with respect to the cannula.

10. The constraint arrangement of claim 1, wherein the feature is a fenestration.

11. The constraint arrangement of claim 1, wherein the feature is a scalloped region.

12. The constraint mechanism of claim 1, wherein the surface is an outside surface.

13. A constraint arrangement for a stent-graft loaded onto a delivery system, the stent-graft having a graft defining an elongate lumen, a plurality of stents and at least one positionable region adjacent to a feature, the delivery system having a cannula and a release wire, the constraint arrangement comprising:
    a first suture extending circumferentially around a surface of the graft from a first fixed end fixed to the stent-graft to the positionable region, and through the graft and into the lumen and returning out of the lumen to the surface of the graft to a second fixed end fixed to the stent-graft, thereby forming a first loop portion of the first suture within the lumen,
    a second suture extending circumferentially around the surface of the graft from a third fixed end fixed to the stent-graft to the positionable region, and into the lumen and returning out of the lumen to the surface of the graft to a fourth fixed end fixed to the stent-graft, thereby forming a second loop portion of the second suture within the lumen,
    the second loop portion wrapped circumferentially around the cannula such that a second pair of legs of the second loop portion and a first pair of legs of the first loop portion hold the positionable region with respect to the cannula,
    wherein a bight of the second loop portion extends through a gap between the first pair of legs of the first loop portion, and
    wherein the release wire extends through the bight thereby capturing the bight and releasably securing the first loop portion and the second loop portion around the cannula.

14. The constraint arrangement of claim 13 wherein the release wire is retractable from the bight thereby releasing the bight such that the positionable region is not held with respect to the cannula.

15. The constraint arrangement of claim 14, wherein expansion of the stent-graft, when the release wire is in the retracted condition, increases the circumferential length between the fixed end of the first suture and the positionable region thereby creating tension in the first suture, the tension acting to retract the first loop portion towards an inner surface of the graft.

16. The constraint arrangement of claim 13, wherein the feature is a fenestration.

17. The constraint arrangement of claim 13, wherein the feature is a scalloped region.

18. A constraint arrangement for a stent-graft loaded onto a delivery system, the stent-graft having a graft defining an elongate lumen, a plurality of stents and at least one positionable region adjacent to a fenestration, the delivery system having a cannula and a release wire, the constraint arrangement comprising:

at least one suture extending at least partially circumferentially around a surface of the graft from a first fixed end fixed to the stent-graft to the positionable region, and through the graft at a first constraining perforation into the lumen and returning out of the lumen to the surface of the graft at a second constraining perforation to a second fixed end fixed to the stent-graft and circumferentially spaced from the first fixed end, thereby forming a loop portion of the at least one suture within the lumen, the loop portion wrapped circumferentially around the cannula such that a pair of legs of the loop portion hold the positionable region with respect to the cannula, wherein a bight of the loop portion extends through a gap between the legs and wherein the release wire extends through the bight thereby capturing the bight and releasably securing the loop portion around the cannula.

19. The constraint mechanism of claim 18, wherein the at least one suture comprises first and second sutures spaced longitudinally from each other, wherein the second suture extends at least partially circumferentially around a surface of the graft from a first fixed end fixed to the stent-graft to the positionable region, and through the graft at a first constraining perforation into the lumen and returning out of the lumen to the surface of the graft at a second constraining perforation to a second fixed end fixed to the stent-graft and circumferentially spaced from the first fixed end, thereby forming a second loop portion of the at least one suture within the lumen, the second loop portion wrapped circumferentially around the cannula such that a second pair of legs of the second loop portion hold the positionable region with respect to the cannula, wherein a bight of the second loop portion extends through a gap between the second pair of legs and wherein the release wire extends through the bight thereby capturing the bight and releasably securing the second loop portion around the cannula.

20. The constraint mechanism of claim 18, wherein the first suture is proximal of the fenestration and the second loop portion is distal of the fenestration.

* * * * *